United States Patent [19]
Cotter

[11] Patent Number: 5,628,726
[45] Date of Patent: May 13, 1997

[54] BLOOD COLLECTION SYSTEM

[75] Inventor: Robert F. Cotter, Duxbury, Mass.

[73] Assignee: Duxbury Scientific, Inc., Hingham, Mass.

[21] Appl. No.: 389,928

[22] Filed: Feb. 16, 1995

[51] Int. Cl.⁶ .................................................. A61M 37/00
[52] U.S. Cl. .......................... 604/4; 137/614.04; 604/905
[58] Field of Search .................... 251/149.1; 137/614.04; 604/4, 905

[56] References Cited

U.S. PATENT DOCUMENTS

| | | |
|---|---|---|
| 4,850,964 | 7/1989 | Cotter et al. . |
| 4,911,194 | 3/1990 | Lechner ........................ 137/614.04 |
| 5,002,529 | 3/1991 | Cunningham . |
| 5,052,725 | 10/1991 | Meyer et al. . |
| 5,201,552 | 4/1993 | Hohmann ..................... 285/308 |
| 5,232,020 | 8/1993 | Mason ......................... 137/614.04 |
| 5,316,041 | 5/1994 | Ramacier ..................... 137/614.04 |
| 5,380,314 | 1/1995 | Herweck ........................... 604/4 |
| 5,406,980 | 4/1995 | Allread ......................... 285/319 |
| 5,431,641 | 7/1995 | Grozinger ...................... 604/905 |
| 5,452,924 | 9/1995 | Kujawski ...................... 285/308 |
| 5,464,042 | 11/1995 | Haunhorst ................... 137/614.04 |
| 5,467,806 | 11/1995 | Stricklin ...................... 137/614.04 |
| 5,492,147 | 2/1996 | Challender ..................... 604/905 |

Primary Examiner—Michael J. Milano
Attorney, Agent, or Firm—George W. Neuner

[57] ABSTRACT

A system for collecting blood including first and second containers and coupling for joining the containers together, the coupling adapted to hold the bags locking the containers together in two different locked positions both positions preventing contamination and one of said locked positions permitting flow of blood between containers.

7 Claims, 5 Drawing Sheets

BLOOD COLLECTION SYSTEM

BACKGROUND OF THE INVENTION

This invention is directed to a new and improved blood collection system.

The collection of a patients own blood has become widely used during surgical procedures and quite often after surgical procedures.

The collected patients blood is reinfused into the patient rather than using the blood from donees which may be diseased.

Examples of prior products for collecting blood are shown and described in U.S. Pat. Nos. 4,850,964 and 5,002,529 as well as in the cited patents therein.

BRIEF DESCRIPTION OF THE INVENTION

The present invention is an improvement over the prior art in that it permits blood to be easily collected in a first container and then transferred as required to a second container which can be used to reinfuse the blood into a patient.

This invention permits the second container to be coupled to the first container in a first position such that the pathway between containers is sealed from contamination prior to transfer of blood from one container to another and then moved into a second sealing position in the same coupling member to permit transfer of blood from one container to another. This invention because of the construction thereof permits the quick automatic closure of the opening to both containers when they are separated from one another.

Because of the construction of this system, it readily lends itself to use by hospital staff and makes handling of blood even if contaminated, less dangerous than usual.

The construction herein of the system also permits a less costly alternative system to be used in place of current technology.

In this system, there is employed a new and improved coupling system and cooperating valving which permits the aforementioned to be accomplished.

For background into a prior art coupling, reference should be had to U.S. Pat. No. 5,052,725.

DETAILED DESCRIPTION OF THE INVENTION

Figure 1:
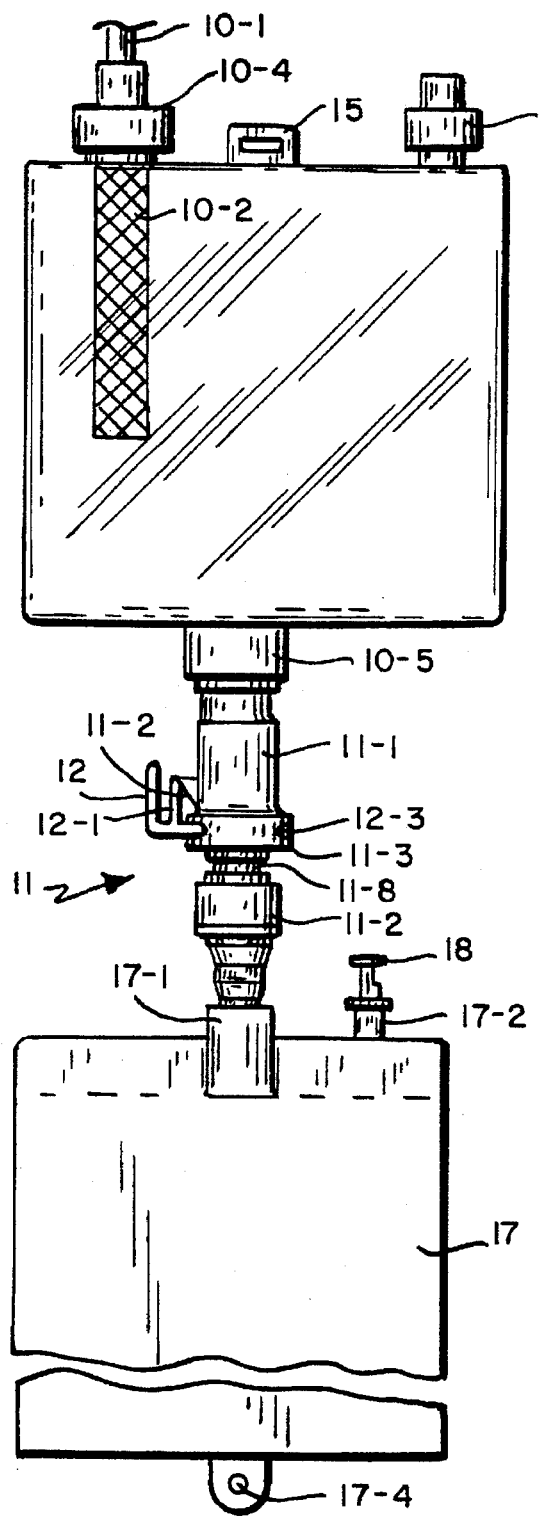
FIG. 1 is a front view of the blood collection system of this invention.
Figure 2:
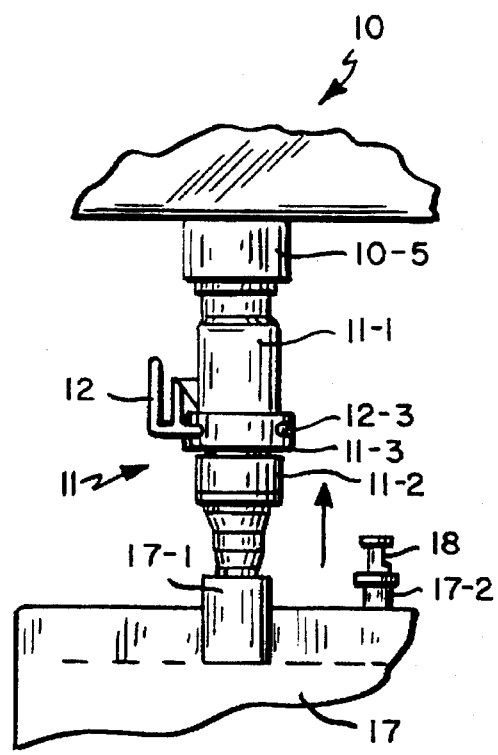
FIG. 2 is a partial view of the blood collection system in which the bags are moved relatively closer to one another in comparison to FIG. 1 in order to permit blood to flow from one container thereof into the other.

Reference should be had to FIGS. 1 and 2 for a description of the invention.

FIG. 1 shows a container 10, preferably a rigid plastic container 10, for collecting blood. The blood is collected through tubing 10-1 positioned in a coupling projection 10-4 attached to the container and defining an opening. The blood is then passed through a conventional mesh filter 10-2. In some cases suction is applied through tubing and coupling 10-3 to cause the blood to flow into the container 10. Another port may be provided, if desired, in the container 10 to inject anticoagulant. At 10-5 is an opening extending from the bottom of the container 10 into which there is positioned and adhesively joined thereto one female coupling member 11-1 of a two piece preferably plastic coupling 11. Within the female coupling member 11-1, there is provided a valve assembly as will be described later with reference to FIGS. 3 to 5 for preventing the flow of blood out of the container 10, except under certain circumstances.

The female coupling 11-1 includes lever 12 assembly which is resiliently biased to the left of FIG. 1 by projection cam 11-2 which engages flexible finger 12-1.

The lever 12 is supported in opening 11-3 and includes a portion 12-3 which is used to lock the male connector 14 in one of two positions within the female connector as will be described.

The container 10 is usually held in a vertical upright position by use of a strap (not shown) placed through the opening in the projection 15 so that gravity flow of blood from one container to another may take place.

At 17, there is shown a container (bag) preferably of flexible plastic which has openings 17-1 and 17-2 at the top thereof.

In the opening 17-1, there is provided a male coupling member 11-2 joined thereto by adhesive.

The male coupling member as shown includes locking grooves, one of which is shown at 11-8. The other of the locking grooves (stops) on the connector is not seen in FIG. 1 since the male coupling is locked in place in a first position in a first groove (stop) in the female coupling, in a locking sealed position.

The bag 17 has the second tube 17-2 adhesively joined thereto for permitting blood in the bag 17 to be reinfused by gravity flow by hanging up the bag by a hook positioned in member 17-4 at the bottom thereof. A removable cap 18 is provided to seal the tube 17-2.

FIG. 2 illustrates the bag 17 moved to a second locked position by relatively moving the two containers 10 and 17 closer together. In this position, the locking portion 12-3 enters the groove 11-8 to lock the bags in the second locking position relative to one another. In this construction as will be described, valves are then opened to each of the bags so that blood may be transferred therebetween.

To separate the containers from one another, the lever is pushed from the left to right of FIGS. 1 and 2, to unlock the containers and allow them to be separated.

Figure 3:
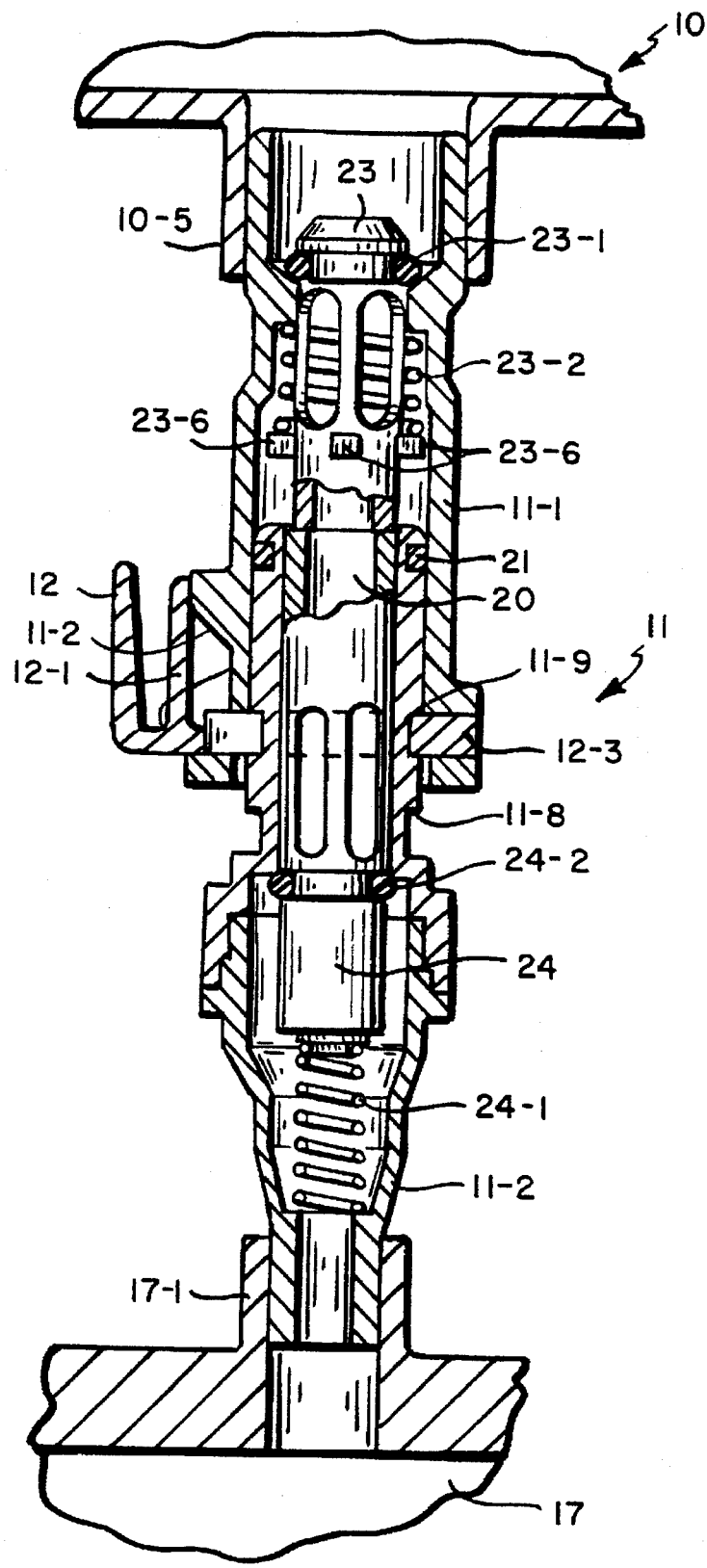
FIG. 3 is a sectional view of the valves and coupling positioned as shown in FIG. 1.

Reference should now be had to FIG. 3 which shows the valves associated with the coupling 11. FIG. 3 illustrates the container 17 and 10 locked in a first position relative to one another and coupled together with the hollow passageway 20 between containers sealed by the coupling and the O-ring 21 supported by the male coupling member 11-2. The locking of the coupling is the result of locking member 12-3 supported by the female coupling 11-1 being positioned in groove 11-9 of the male coupling member 11-2. The locking member is retained therein by action of the flexible spring like member 12-1 which because of its plastic memory urges said lever 12 to the left of FIG. 2 after being bent to the left of FIG. 2 by its return to an upright position caused by its action against projection 11-2. The valve 23 is closed when the coupling is locked in place as shown in FIG. 3.

As shown, the valve 23 is urged to a closed position by spring 23-2 supported by rib members 23-6.

The female coupling member supports a valve 23 having a sealing O-ring 23-1.

At 24, there is shown a second valve, which has a spring 24-1 and a sealing O-ring 24-2. As shown in FIG. 3, the valve 24 is closed.

Thus, fluid (blood) is prevented from passing between containers 10 and 17.

Figure 4:
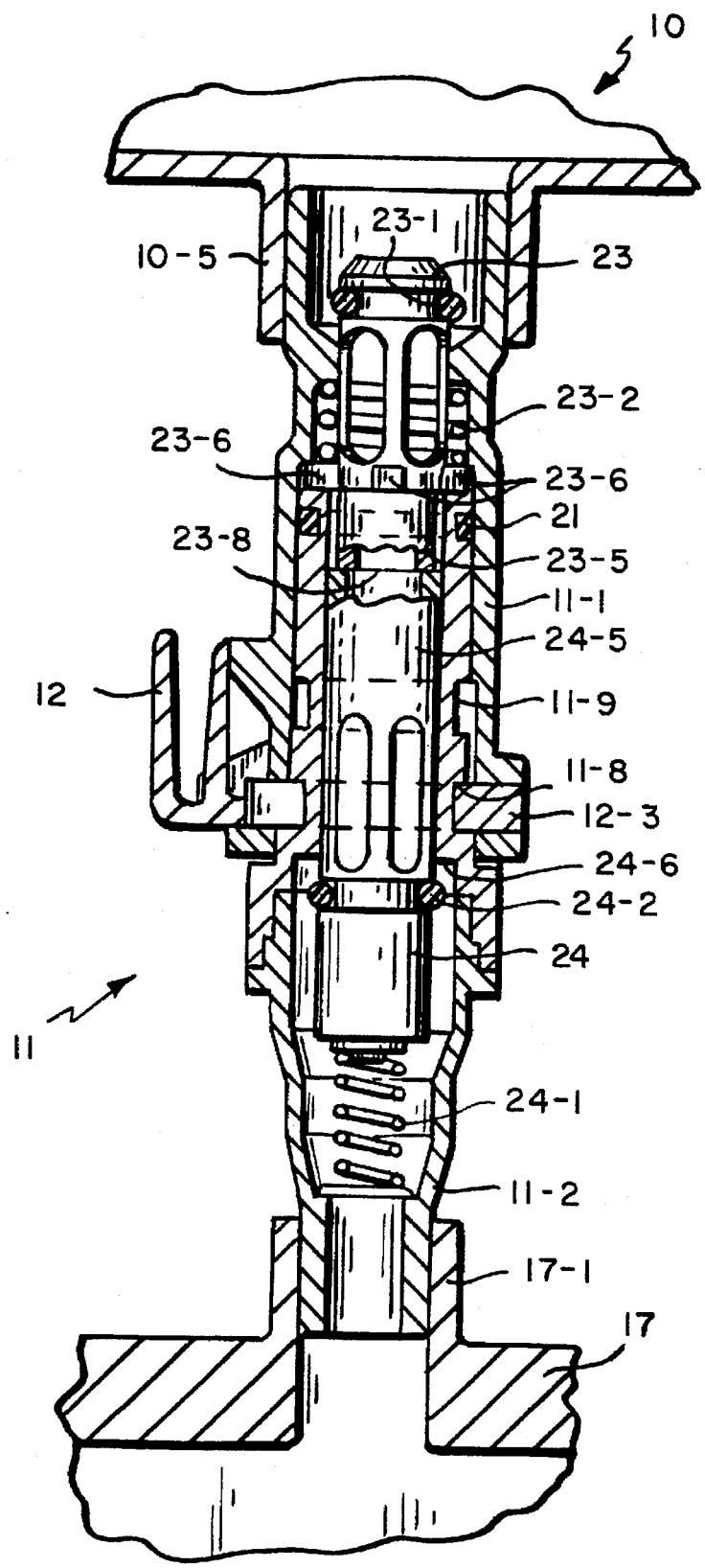
FIG. 4 is a sectional view of the valves and coupling positioned as shown in FIG. 2.

Reference should now be had to FIG. 4 which shows the containers moved to a second locked position with the locking member 12-3 is positioned within groove 11-8.

In FIG. 4, the valves 23 and 24 are opened as the movable sleeve 24-5 coupled to the valve 24 engages the member 23-5 of valve 23 at 23-8 which urges the O-ring 23-1 away from the valve seat 23-6 and at the same time due to resistance of the spring 23-2 causes the O-ring 24-2 away from valve seat 24-6. Thus blood can flow in passageway 20 between containers 10 and 17.

Figure 5:
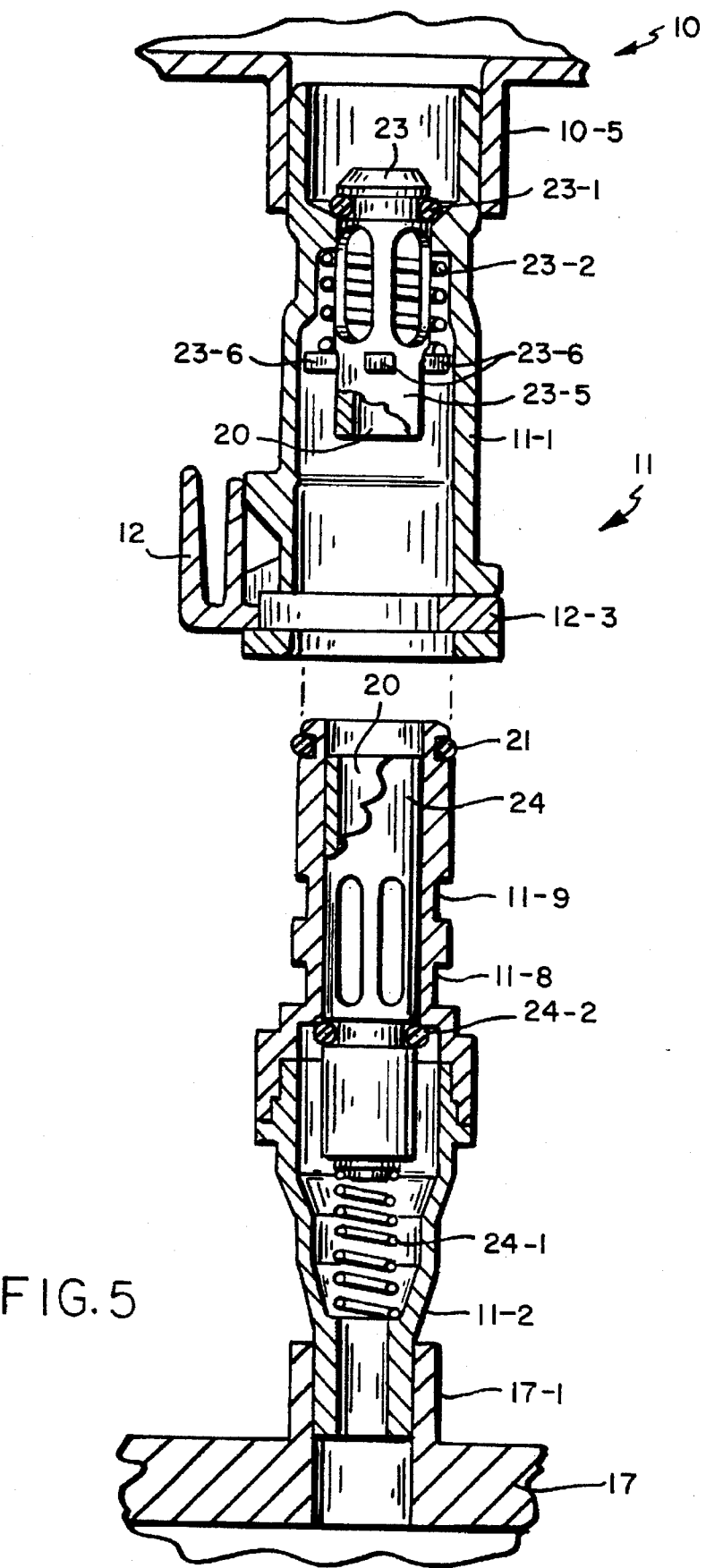
FIG. 5 shows the valving and coupling in the position when the containers are separated.

FIG. 5 illustrates the coupling 11-1 and 11-2 separated which is accomplished by pushing lever 12 to the right of FIG. 5 to release the containers.

It should be understood because of the construction herein it is possible to connect the containers together in a sealed bag so that the user merely takes out the system and hangs it up for the future collection of blood since the containers are already coupled and sealed together as shown in FIG. 3. When the user e.g. nurse wants to collect blood, for reinfusion or for disposal, the coupling is locked into position shown in FIG. 4 for collection of blood.

Figure 6:
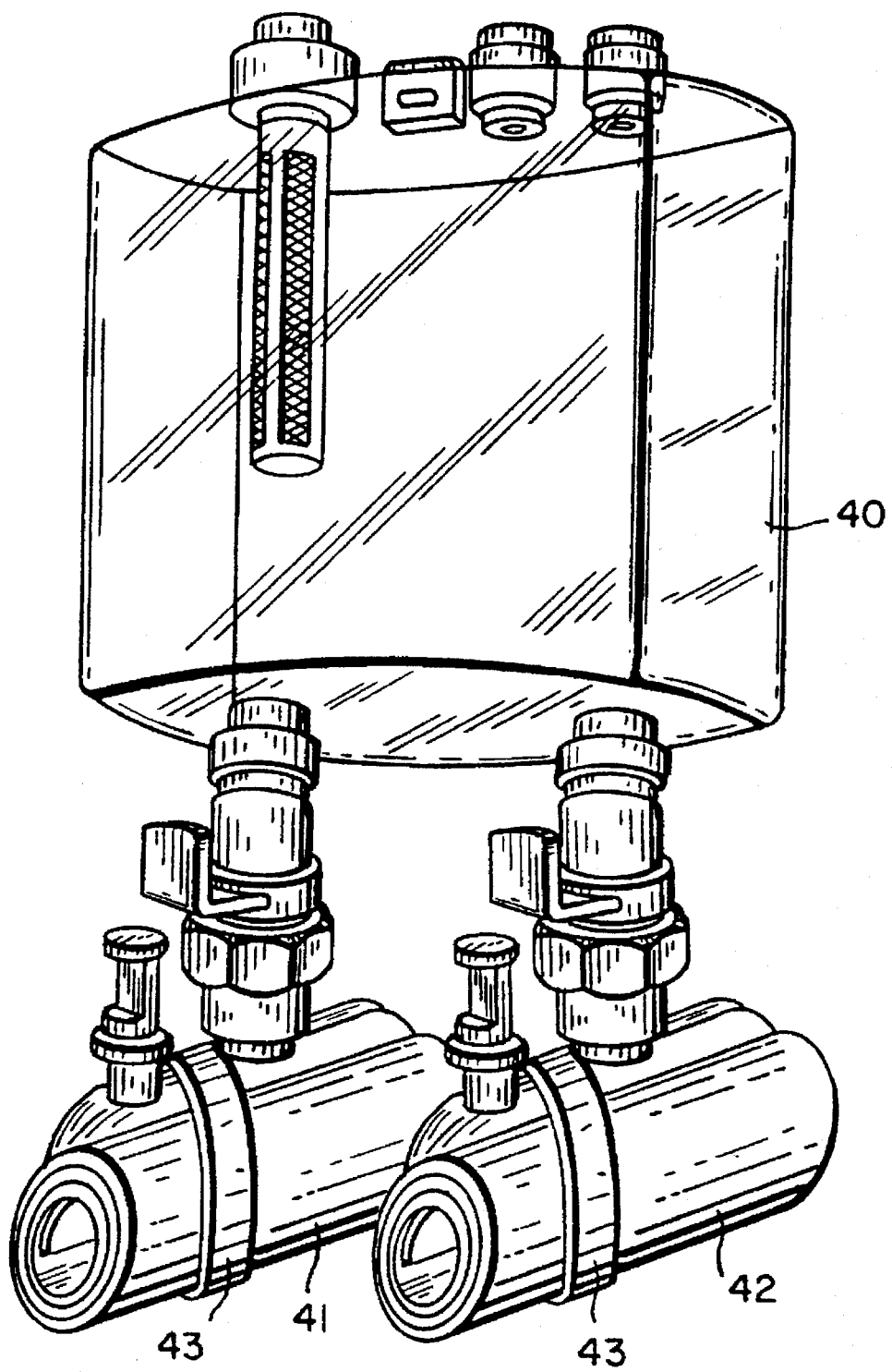
FIG. 6 shows in perspective, a modified system for two containers to be filled from a single container.

In FIG. 6, there is shown a double system comprising first container 40 with rolled up bags (containers) 41 and 42, both bags 41 and 42 coupled through the same coupling as shown in FIGS. 1 to 5. The plastic straps 43 holding the bags in a rolled positioned are removed e.g. unhooked or cut to let the bag 41 and 42 unroll and collect blood.

I claim:

1. A blood collection system comprising a first container for collecting blood, a second container for receiving blood from said first container, a coupling having a female coupling portion containing a first valve and a male coupling portion containing a second valve, said coupling connected to said first and second containers respectively, said coupling holding said first and second containers together in a first locked position with the valves thereof closed preventing flow of blood between one container and another while preventing contamination of the blood passageway between the containers and when the containers are moved relatively closer together to a second locked position and held in place causing the opening of the valves for the both containers to permit the flow of blood between the containers, wherein relative rotation between the female coupling portion and the male coupling portion does not provide relative axial movement therebetween.

2. A blood collection system comprising a first container for collecting blood, a second container for receiving blood from said first container, a coupling having a female coupling portion containing a first valve and a male coupling portion containing a second valve, said coupling connected to said first and second containers respectively, said coupling holding said first and second containers together in a first locked position with the valves thereof closed preventing flow of blood between one container and another while preventing contamination of the blood passageway between the containers and when the containers are moved relatively closer together to a second locked position and held in place causing the opening of the valves for the both containers to permit the flow of blood between the containers, and in which said coupling includes a first stop and a second stop, and a moveable member to engage said first and second stops to lock said connector in said first and second positions.

3. The system according to claim 2 in which said first and second stops are positioned on the male coupling portion of said coupling.

4. The system according to claim 3 in which each of said stops comprises a groove positioned on said male coupling portion and wherein male coupling portion is locked in place by said movable member which is supported by said female coupling portion.

5. A system for collecting blood and transferring same for reinfusion or other purposes comprising a first container, a second container, a third container, said second and third containers each coupled to a said first container by a coupling means, each said coupling means including means for locking said second or third container in a first position while maintaining a contamination free pathway between said second or third container and said first container, and means for locking said second or third container in a second position while maintaining a contamination free pathway between said second or third container and said first container, valve means associated with said coupling means between said first and second containers and between said first and third containers, said valve means being opened between said first and second container and said first and third containers by said coupling means when said coupling means are locked in said second position, wherein relative rotation of said containers coupled by each said coupling means does not provide relative axial movement therebetween.

6. A container for collecting samples, said container comprising an integrally connected female coupling member having a passageway containing a valve assembly with a valve in a normally closed position and connected to the female coupling member a male coupling member;

said female coupling member adapted to receive said male coupling member having a passageway containing a valve assembly with a valve in a normally closed position, wherein the female coupling member and the male coupling member provide a contamination free pathway between opposing ends of a coupling formed thereby;

said male member having a first locking groove that cooperates with the female member to lock the male member and the female member together in a first position wherein both valves remain closed to seal the passageway;

said male member having a second locking groove that cooperates with the female member to lock the male member and the female member together in a second position wherein the opposing ends of the coupling are closer together and both valves are open, thereby opening the passageway between opposing ends of the coupling.

7. A container for collecting samples, said container comprising an integrally connected male coupling member having a passageway containing a valve assembly with a valve in a normally closed position;

said male coupling member adapted to receive a female coupling member having a passageway containing a valve assembly with a valve in a normally closed position, wherein the female coupling member and the male coupling member provide a contamination free pathway between opposing ends of a coupling formed thereby;

said male member having a first locking groove that cooperates with the female member to lock the male member and the female member together in a first position wherein both valves remain closed to seal the passageway;

said male member having a second locking groove that cooperates with the female member to lock the male member and the female member together in a second position wherein the opposing ends of the coupling are closer together and both valves are open, thereby opening passageway is open between opposing ends of the coupling.

* * * * *